United States Patent
Bullen et al.

(10) Patent No.: US 7,182,915 B2
(45) Date of Patent: Feb. 27, 2007

(54) PIPETTE CONFIGURATIONS AND ARRAYS THEREOF FOR MEASURING CELLULAR ELECTRICAL PROPERTIES

(75) Inventors: Andrew Bullen, Wallingford, CT (US); Charles David Weaver, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 592 days.

(21) Appl. No.: 10/305,801

(22) Filed: Nov. 27, 2002

(65) Prior Publication Data

US 2003/0132109 A1    Jul. 17, 2003

Related U.S. Application Data (60) Provisional application No. 60/338,538, filed on Nov. 30, 2001.

(51) Int. Cl.
*B01L 3/02* (2006.01)
*G01N 1/14* (2006.01)

(52) U.S. Cl. .................. 422/100; 422/922; 422/936; 73/863.32; 73/864; 73/864.01

(58) Field of Classification Search .............. 422/100, 422/922, 924, 936, 930; 73/863.32, 863.64, 73/864, 864.01; 604/261, 263, 264; 128/919
See application file for complete search history.

(56) References Cited

U.S. PATENT DOCUMENTS

| | | | | |
|---|---|---|---|---|
| 605,146 A | * | 6/1898 | Stokes | 73/864.01 |
| 936,757 A | * | 10/1909 | Butts, Jr. | 73/864.01 |
| 1,547,562 A | * | 7/1925 | Byrd | 422/100 |
| 1,662,682 A | * | 3/1928 | Lloyd | 604/217 |
| 1,713,937 A | * | 5/1929 | Wheeland | 604/299 |
| 2,172,575 A | * | 9/1939 | Caulfield | 73/864.15 |
| 2,237,213 A | * | 4/1941 | Brown | 73/864.02 |
| 2,321,369 A | * | 6/1943 | William | 604/217 |

(Continued)

FOREIGN PATENT DOCUMENTS

WO      WO 98/50791      11/1998

(Continued)

*Primary Examiner*—Brian R. Gordon
(74) *Attorney, Agent, or Firm*—Brian C. Carey; Briana C. Bergen (57) ABSTRACT

The present application is directed to pipette configurations, arrays of the same and methods for using such pipettes and arrays to accomplish electrical measurements, including whole cell and on cell measurements. In one aspect of the present invention, a pipette includes a hollow tubular section having a distal portion and a tip portion. A bubble is formed at the tip and includes an interior chamber in communication with the hollow tubular section at an end adjacent to the bubble portion. The bubble may have a diameter greater than the diameter of an adjacent portion of the hollow tubular section. An aperture is formed between the internal chamber and an exterior surface of the bubble to accommodate seal formation. In a second aspect of the present invention, a method for forming a glass pipette of the present invention is provided which includes the following steps: (1) heating a glass tube, (2) pulling the glass tube to form a blunt tip, (3) heating the blunt tip, and (4) applying back pressure from the tube to form a bubble including an aperture from the blunt tip.

46 Claims, 12 Drawing Sheets

U.S. PATENT DOCUMENTS

| | | | | |
|---|---|---|---|---|
| 2,330,149 | A | * | 9/1943 | Schaaff .................... 222/158 |
| 2,358,159 | A | * | 9/1944 | Gruetter .................... 604/310 |
| 3,834,241 | A | | 9/1974 | Garren et al. |
| 4,022,576 | A | * | 5/1977 | Parker ...................... 436/177 |
| 4,118,195 | A | * | 10/1978 | Beach ....................... 222/215 |
| 4,197,745 | A | | 4/1980 | Kumbrant |
| 4,212,204 | A | * | 7/1980 | St. Amand ............... 73/864.11 |
| 4,396,024 | A | * | 8/1983 | Sarstedt .................... 600/576 |
| 4,563,104 | A | * | 1/1986 | Saint-Amand ............. 401/139 |
| 4,563,332 | A | * | 1/1986 | Mitchell et al. ............ 422/100 |
| 4,779,768 | A | * | 10/1988 | St. Amand ................. 222/209 |
| 4,806,313 | A | * | 2/1989 | Ebersole et al. .............. 422/61 |
| 4,808,381 | A | * | 2/1989 | McGregor et al. .......... 422/100 |
| 4,840,272 | A | * | 6/1989 | Goldman .................... 206/365 |
| 4,885,945 | A | * | 12/1989 | Chiodo .................... 73/863.32 |
| 4,981,654 | A | * | 1/1991 | Kuntz et al. ................. 422/102 |
| 5,007,287 | A | * | 4/1991 | Nagai ....................... 73/290 B |
| 5,073,347 | A | * | 12/1991 | Garren et al. ............... 422/100 |
| 5,120,321 | A | * | 6/1992 | Oksman et al. ............. 604/198 |
| 5,226,572 | A | * | 7/1993 | Gargione .................... 222/214 |
| 5,230,864 | A | | 7/1993 | Columbus .................. 422/100 |
| 5,318,547 | A | * | 6/1994 | Altschuler .................. 604/198 |
| 5,385,557 | A | * | 1/1995 | Thompson .................. 604/198 |
| 5,406,856 | A | | 4/1995 | Kuhn |
| 5,415,645 | A | * | 5/1995 | Friend et al. ................ 604/110 |
| D401,698 | S | * | 11/1998 | Daniels ..................... D24/222 |
| 6,063,260 | A | | 5/2000 | Olesen et al. |
| 6,101,946 | A | * | 8/2000 | Martinsky .................... 101/494 |
| 6,117,291 | A | | 9/2000 | Olesen et al. |
| 6,213,987 | B1 | * | 4/2001 | Hirsch et al. ................ 604/263 |
| 6,343,717 | B1 | * | 2/2002 | Zhang et al. ................ 222/209 |
| 6,361,744 | B1 | * | 3/2002 | Levy ............................ 422/99 |
| 6,401,552 | B1 | * | 6/2002 | Elkins ........................... 73/863 |
| 6,457,612 | B1 | * | 10/2002 | Zhang et al. ............. 222/465.1 |
| 6,531,098 | B1 | * | 3/2003 | Kenney ...................... 422/100 |
| 6,589,484 | B2 | * | 7/2003 | Buehler ...................... 422/100 |
| 6,641,993 | B1 | * | 11/2003 | Jacobs et al. ................... 435/4 |
| 2002/0025568 | A1 | | 2/2002 | Maher et al. |
| 2002/0057996 | A1 | * | 5/2002 | Bass .......................... 422/102 |
| 2002/0063067 | A1 | | 5/2002 | Bech et al. |
| 2002/0064841 | A1 | | 5/2002 | Kiemic et al. |
| 2002/0144905 | A1 | | 10/2002 | Schmidt |
| 2003/0125677 | A1 | * | 7/2003 | Swenson et al. ............ 604/263 |
| 2004/0019332 | A1 | * | 1/2004 | Grabis et al. ................ 604/198 |
| 2004/0019334 | A1 | * | 1/2004 | Ohkubo et al. .............. 604/263 |
| 2004/0039333 | A1 | * | 2/2004 | Lee et al. .................... 604/110 |
| 2004/0249351 | A1 | * | 12/2004 | Hongo et al. ............... 604/263 |
| 2006/0020245 | A1 | * | 1/2006 | Teringo ...................... 604/263 |
| 2006/0111677 | A1 | * | 5/2006 | Nesbitt ....................... 604/192 |

FOREIGN PATENT DOCUMENTS

| | | |
|---|---|---|
| WO | WO 99/66329 | 12/1999 |
| WO | WO 00/34776 | 6/2000 |

* cited by examiner

PIPETTE CONFIGURATIONS AND ARRAYS THEREOF FOR MEASURING CELLULAR ELECTRICAL PROPERTIES

CROSS-REFERENCE TO RELATED APPLICATION

This application claims priority to U.S. Provisional Patent Application No. 60/338,538, filed Nov. 30, 2001.

FIELD OF THE INVENTION

The present invention relates generally to measuring and testing and, more particularly, to a pipette or an array of pipettes for measuring cellular electrical properties including ion channel currents, membrane potential, transporter flux and cell capacitance.

BACKGROUND OF THE INVENTION

Ion channel measurement plays an important role in determining the effect of compounds and the like at the cellular level. Ion channels are transmembrane proteins that form pores in a cell membrane, which, in turn, allow ions to pass from one side of the cell membrane to another. The activity of these channels influences cell membrane potential and are responsible for mediating changes in overall cell excitability.

Patch clamp techniques are commonly used for performing ion channel measurements. Certain patch clamp techniques are described in Sakmann and Neher, "Single-Channel Recording," Plenum, 1995. Typically, such techniques involve the use of a glass pipette or micropipette to contact with, and ideally attach to, a cell. A conventional micropipette for patch clamp recording is a hollow glass tube having a polished blunt tip and an aperture therethrough. Other micropipette types, such as sharp electrodes, are employed in other types of electrophysiology. Sharp microelectrodes typically impale cells rather than forming tight seals with the membrane. Methodologies for forming micropipettes are disclosed in Brown and Flaming, "Advanced Micropipette Techniques for Cell Physiology", 1989, and a cross-section of a blunt tip of a prior art micropipette is displayed in FIG. 1.

To have the micropipette contact with, and attach to, the cell, standard cell location and pipette placement techniques may be used. Alternatively, the cell may be positioned, for example, at the aperture of the micropipette by manipulating an electric field via an electrode positioned in proximity to the aperture. A critical step in any patch clamp recording process is the formation of an acceptable seal between the outside surface or inner rim of the blunt tip of the micropipette and the attached cell. An acceptable seal is often referred to as a "giga-ohm seal" because it generally demonstrates electrical resistance measurable in giga-ohms. (Reference herein to forming a "seal" shall mean the formation of an electrically acceptable seal having sufficient electrical resistance to be measurable; it is preferred that the electrical resistance be greater than or equal to 1 giga-ohm, but may be less than.) Conventional techniques are known for forming a seal.

After seal formation, it is often desired to obtain "whole cell" access which is achieved via electroporation, additional negative pressure, chemopermeabilization or a combination thereof. (Mere attachment of the micropipette, even in a sealed state, to the cell provides a limited "on cell" configuration which can be used to measure ion channel properties from the small patch of membrane under the electrode). Test compounds and the like may then be applied to the cell, and changes in its electrical properties (i.e., current, potential, conductance and capacitance) may thereafter be measured. These measurements, in turn, can be used to assay ion channel activity, transporter activity, or changes in the properties of cell membrane caused by cell-to-cell interactions, cell-to-cell fusion, viral infection, endocytosis, exocytosis, membrane cycling and membrane-to-ligand interactions.

Various patch clamp techniques employing blunt tip micropipettes are disclosed in U.S. Pat. No. 6,063,260 and PCT Publication Nos. WO 98/50791, WO 99/66329 and WO 00/34776.

Figure 1:
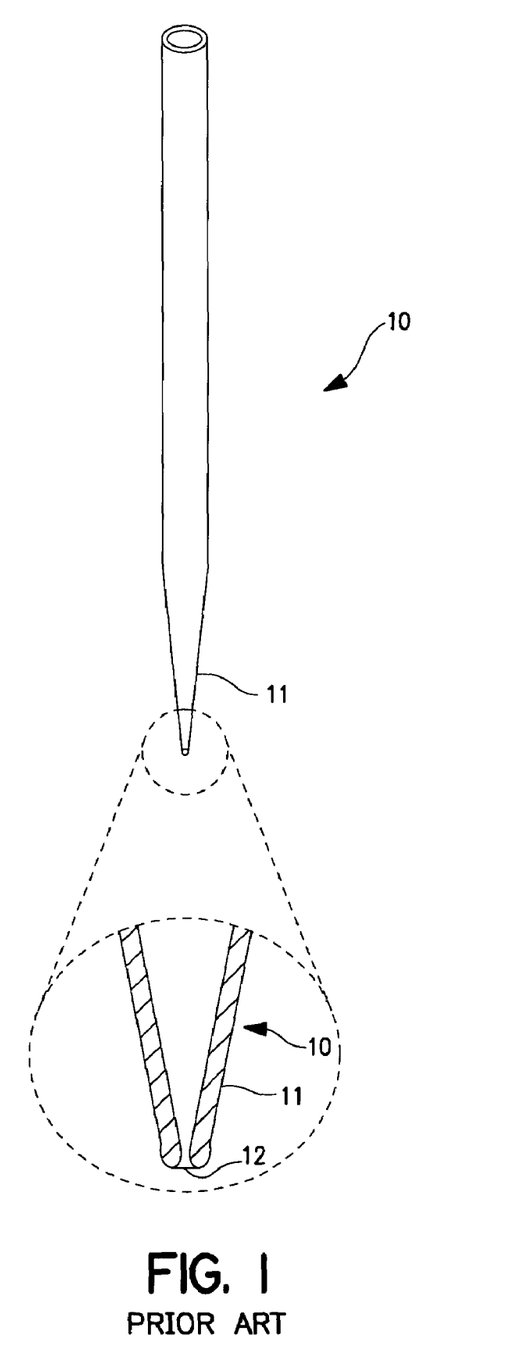
FIG. 1 illustrates a blunt tip pipette and an enlarged cross-sectional view of the tip thereof.

FIG. 1 displays an entire blunt tip pipette 10 and an enlarged cross-section of the tip thereof, as found in conventional technologies. The pipette 10 typically has an aperture 12 disposed at the tip 11 thereof. Such pipettes 10 are typically composed of a glass. To perform patch clamping, the aperture 12 is positioned to contact a subject cell. In the prior art, the act of positioning the micropipette tip is tedious, requiring initial cell location (e.g., on a dish, in a cell bath); and, positioning the micropipette properly relative to the located cell. With prior art techniques, the processes of cell location and micropipette positioning are manually achieved, typically using a high quality microscope, and a high quality three axis micromanipulator (with sub-micro resolution in each axis and a high degree of stability) to control location of the micropipette tip. As is readily appreciated, the skill of the operator determines the speed and efficiency by which patch clamping can be conducted. Techniques have been developed to facilitate the cell contacting, such as with introducing a slight electrical field at the tip of the micropipette. In addition, techniques have been developed which, through automation, allow for repeated cell location and proper micropipette positioning, such as a technique disclosed in WIPO International Publication Number WO 00/34776; and a technique disclosed in copending U.S. patent application Ser. No. 60/338,715 the inventors and assignee herein. Upon cell location and contacting, seal formation is achieved using known techniques, and electrophysiological properties of the cell are measured by an electrode or other probe, and associated electronics.

Conventional pipette designs, however, suffer from various drawbacks, including the time required for manual fabrication. Since pipettes cannot be reused, time-consuming fabrication is required individually for each cell to be tested. In addition, conventional pipette designs suffer from propendency to become blocked, difficulty in filling with saline solutions (especially close to the tip) and the limitation that seal formation must occur outside the pipette. Similarly electrical measurement can be distorted by the unfavorable electrical properties arising from the narrow opening of blunt tip pipettes. In addition, the processes of cell contacting, attachment, seal formation and electrical measurement require advanced and detailed steps that are not readily amenable to automation. Thus, a high degree of skill is required to perform patch clamp techniques using existing technologies. Accordingly, there is a need for new pipette configurations which readily addresses certain problems of the prior art.

SUMMARY OF THE INVENTION

The present application is directed to pipette configurations, arrays of the same and methods for using such pipettes and arrays to accomplish electrical measurements, including whole cell and on cell measurements. (As used herein, and generally understood in the art, the term "whole cell" refers to a testing configuration where an aperture formed in a micropipette is in communication with a hole that extends through the lipid bi-layer (i.e., membrane) of a cell such that electrophysiological data obtained during testing result from the cell's entire plasma membrane, and its constituent ion channels and/or electrogenic transporters, thus, the "whole" cell. As used herein, and generally understood in the art, the term "on cell" refers to a testing configuration where an aperture formed in a micropipette does not communicate with the interior of a cell (i.e., the micropipette contacts partially or wholly intact membrane).) In one aspect of the present invention, a pipette includes a hollow tubular section having a distal portion and a tip portion. A bubble is formed at the tip and includes an interior chamber in communication with the hollow tubular section at an end adjacent to the bubble portion. The bubble may have a diameter greater than the diameter of an adjacent portion of the hollow tubular section. An aperture is formed between the internal chamber and an exterior surface of the bubble to accommodate seal formation.

Additionally, in certain embodiments, a second guard pipette may be disposed about the micropipette such that the bubble is at least partially covered on the side. The guard pipette may be rigidly fixed to the micropipette, or, alternatively, be allowed to slide relative to the micropipette. A cup-shaped reservoir is collectively defined by the guard pipette and the micropipette about the bubble. The reservoir may be used for assaying compounds.

In a second aspect of the present invention, a method for forming a glass pipette of the present invention is provided which includes the following steps: (1) heating a glass tube, (2) pulling the glass tube to form a blunt tip, (3) heating the blunt tip, and (4) applying back pressure from the tube to form a bubble including an aperture from the blunt tip. The method may further include the following steps: (5) polishing at least the bubble to accommodate seal formation, and (6) securing a guard pipette to a portion of the glass tube, where the guard pipette has a diameter greater than the glass tube and extends from the glass tube to a point beyond an end of the bubble.

In further aspects of the present invention, methods for screening compounds (whole cell or on cell) in view of cell electrophysiological activity are provided. In a first method, a micropipette, as described above with respect to the first aspect of the subject invention, is used in any manner known to those skilled in the art to obtain an acceptable seal with a cell (preferably in a whole cell configuration) with the cell being introduced to various compounds. The cell may be held stationary in a moving stream of compounds (e.g., in a cell bath), or the cell may be submerged into a well of a compound or compounds. As is readily appreciated by those skilled in the art, conventional electrical measurement techniques (e.g., voltage clamping; current clamping) may be used to obtain data. It is preferred that the guarded assembly be used to facilitate formation of a volume of liquid which encompasses the sealed cell. The volume of liquid is maintained in the reservoir formed at the end of the guarded assembly by surface tension extending across the guard pipette and capillary attraction of the volume of liquid to the walls of the reservoir. The volume of liquid maintains the electrical and mechanical stability of the cell seal by ensuring that the cell does not encounter an air/liquid interface during the course of an experiment.

With a second method, the guarded assembly is used in an inverted position where the bubble is located gravitationally above the distal portion of the pipette. A solution, including cells, is disposed into a cup-shaped reservoir defined by the micropipette and surrounding guard pipette. Upon a cell becoming attached to an aperture of the micropipette, a seal between the cell and an exterior surface of the bubble portion may be formed. One or more compounds or the like may then be applied to the cell through introduction into the reservoir. Electrophysiological testing is conducted as with other methods.

In a third method, the bubble formed on the micropipette may be formed to he relatively large. With the micropipette being in an upright position (the tip of the micropipette being located gravitationally below the bubble), the bubble may act as a well for patch clamping. A cell, or cells, are introduced internally into the bubble through the micropipette, with negative pressure being generated externally of the micropipette and applied to an aperture formed in the tip. Upon a cell settling into the aperture of the tip, an acceptable seal may be conventionally formed and testing conducted thereafter on the sealed cell.

Arrays of similar micropipettes may be provided or constructed in order to perform simultaneous cell measurements in accordance with the methods discussed above.

BRIEF DESCRIPTION OF THE DRAWINGS

Further aspects of the present invention will be more readily appreciated upon review of the detailed description of the preferred embodiments included below when taken in conjunction with the accompanying drawings, of which.

DETAILED DESCRIPTION OF THE INVENTION

With reference to FIGS. 2–12, wherein similar components of the present invention are referenced in like manner, preferred pipette configurations, arrays of pipettes and methods of using the same are disclosed. (The terms "pipette" and "micropipette", in singular and plural, are used interchangeably herein.)

Figure 2:
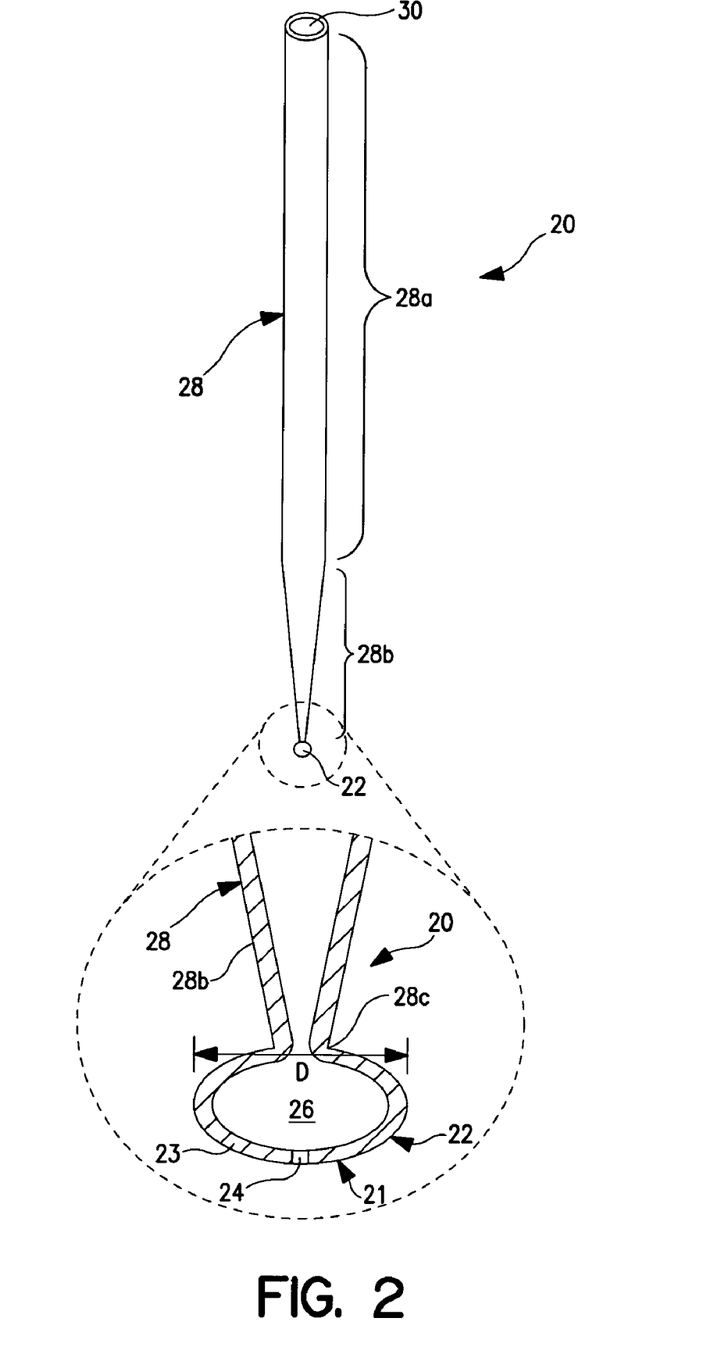
FIG. 2 illustrates a micropipette of the present invention and an enlarged cross-sectional view of the bubble thereof.

FIG. 2 displays a pipette configuration according to the present invention. Referring to FIG. 2, a bubble pipette 20 has a bubble 22 formed at a tip thereof such that an exterior surface 21 forms an end of the pipette 20. The bubble 22 includes an aperture 24 formed through exterior surface 21, which is preferably located at a gravitational low-point (the nadir with the bubble pipette 20 in an upright position) of the exterior surface 21. The bubble 22 is formed by a wall 23, and the wall 23 defines a hollow internal chamber 26 that is in communication with the lumen of a tubular section 28 of the pipette 20. The exterior surface 21 may be planar or, more preferably, is arcuate. The bubble 22 may be substantially spherical or ovuloid in shape, with the internal chamber 26 having a cross-section that is circular or oval, respectively.

The bubble 22 preferably has an outer dimension D (which may be a diameter if the bubble 22 is spherical) of 25 μm or less, and more preferably 5–10 μm. Within this range, the thickness of the wall 23 is approximately 1 μm. As is readily appreciated, the thickness of the wall 23 may increase where the dimension D is smaller.

The hollow tubular section 28 is disposed between an open distal end 30 of the pipette 20 and the bubble 22. The hollow tubular section 28 may include a section 28a of a substantially continuous or equal diameter, and a tapered section 28b connecting the section 28a and the bubble 22. Alternatively, the hollow tubular section 28 may be substantially continuous in diameter throughout (i.e., no tapered section 28b is provided). When referencing the diameter of the hollow tube and the bubble, it should be readily appreciated that the diameter may be an internal diameter (e.g., measured from the interior surface of the relevant section), an exterior diameter (e.g., measured from the exterior surface of the relevant section), or may apply equally to both internal and external diameters.

The bubble 22 is preferably formed dimensionally larger than an adjacent portion of the pipette 20, but may be formed smaller than other portions. For example, with reference to FIG. 2, the bubble 22 is formed with the dimension D which is larger than adjacent portion 28c. However, section 28a may be formed with an outer diameter which is larger than the dimension D. It is not critical to practicing the invention to have the bubble 22 define the largest (cross-sectionally) portion of the pipette 20.

The aperture 24 is an opening which extends through the exterior surface 21 of the bubble 22 and into communication with the interior chamber 26. The aperture 24 is of a size which is substantially smaller than a single cell or portion thereof. Typically, the aperture 24 defines an opening with a dimension between 0.5 and 3 microns. Alternatively, a larger opening may be provided for the aperture 24.

Portions of the exterior surface 21 encircling the aperture 24 are preferably smooth and coextensive with other portions of the exterior surface 21 such that no protruding element or elements are defined about the aperture 24. The pipette 20 may be formed of any acceptable material known to those skilled in the art, including a laboratory-grade borosilicate glass, such as CORNING 7052 or SCHOTT 8250. With the subject invention, a pipette is provided having a bubble tip with an enlarged tip (rather than a limited blunt tip) for contacting with, and allowing for testing of, a subject cell.

Figure 3:
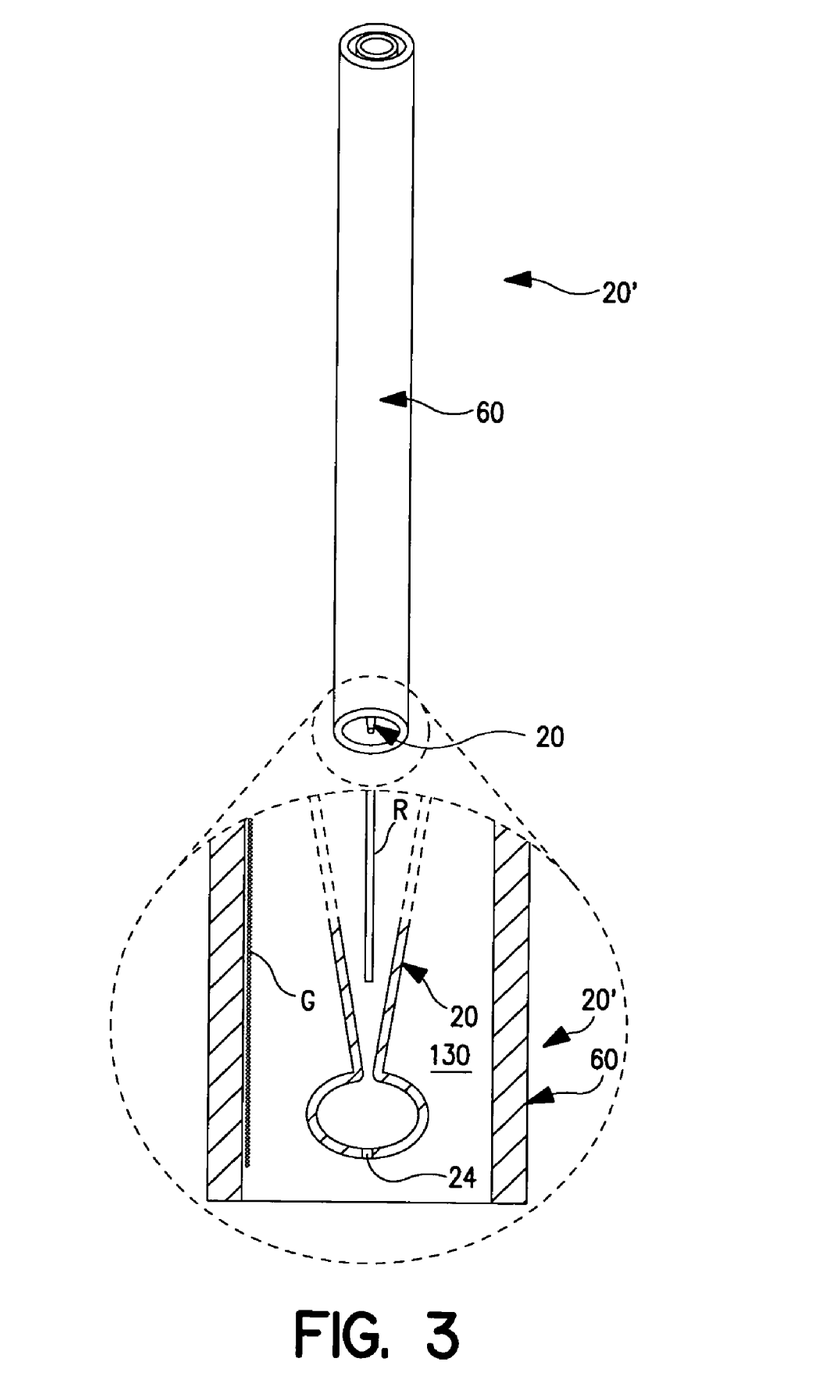
FIG. 3 illustrates a guarded assembly of the present invention and an enlarged cross-sectional view of the tip thereof.

In another aspect of the subject invention, FIG. 3 displays a guarded assembly 20' including a bubble pipette 20 and a guard pipette 60. The guard pipette 60 is tubular and may be of continuous diameter or may have a section of decreasing diameter. The guard pipette 60 is disposed coaxially about the bubble pipette 20, and, preferably, the guard pipette 60 is of a diameter that accommodates secure positioning of the bubble pipette 20 therein. An adhesive or the like may be used to secure the guard pipette 60 to the bubble pipette 20. Alternatively, the guard pipette 60 may be mounted on the bubble pipette 20 in any manner apparent to one of skill in the art. The guard pipette 60 may be made of a similar material as the bubble pipette 20 or other materials not limited to glass. The guard pipette 60 may furthermore accommodate the retention of fluid therein which is in communication with the bubble pipette 20. In preparing the guarded assembly 20', as more fully described below, the guard pipette 60 is slid about the bubble 20 until a predetermined length of the guard pipette 60 is disposed about the bubble 22 of the pipette 20. Preferably, the guard pipette 60 is positioned to at least cover the bubble 22 of the pipette 20, and, more preferably, the guard pipette 60 extends beyond the bubble 22 to define a cup-shaped reservoir to facilitate accommodating a volume of liquid that encompasses the bubble 22. The volume of liquid is maintained within the reservoir of the guard pipette 60 due to surface tension extending across the guard pipette 60 and capillary attraction of the volume of liquid to the guard pipette 60. The volume of liquid maintains the electrical and mechanical stability of the cell seal by ensuring that the cell does not encounter an air/liquid interface during the course of an experiment.

A ground electrode G may be disposed within the guard pipette 60 of the guarded assembly 20'. The ground electrode G may be used to not only monitor electrical properties thereat (relative to the guard pipette 60/guarded assembly 20') but also in concert with a recording electrode R that is disposed within the bubble pipette 20. The recording electrode R and/or the ground electrode G may be used in current clamp and voltage clamp techniques as known to those skilled in the art. The pipette 20 is at least partially filled will saline solution to facilitate testing by the recording electrode R. Alternatively, the ground electrode G can be located externally of the guard pipette 60, such as being attached to an external surface of the guard pipette 60. Being located externally, the ground electrode G should be insulated over a majority of its length with an insulative material, such as a plastic polymeric material (e.g., polytetrafluoroethylene). The ends of the ground electrode G should remain exposed. One end of the ground electrode G may extend into the cup-shaped reservoir defined about the bubble 22 by the guard pipette 60.

Figure 4:
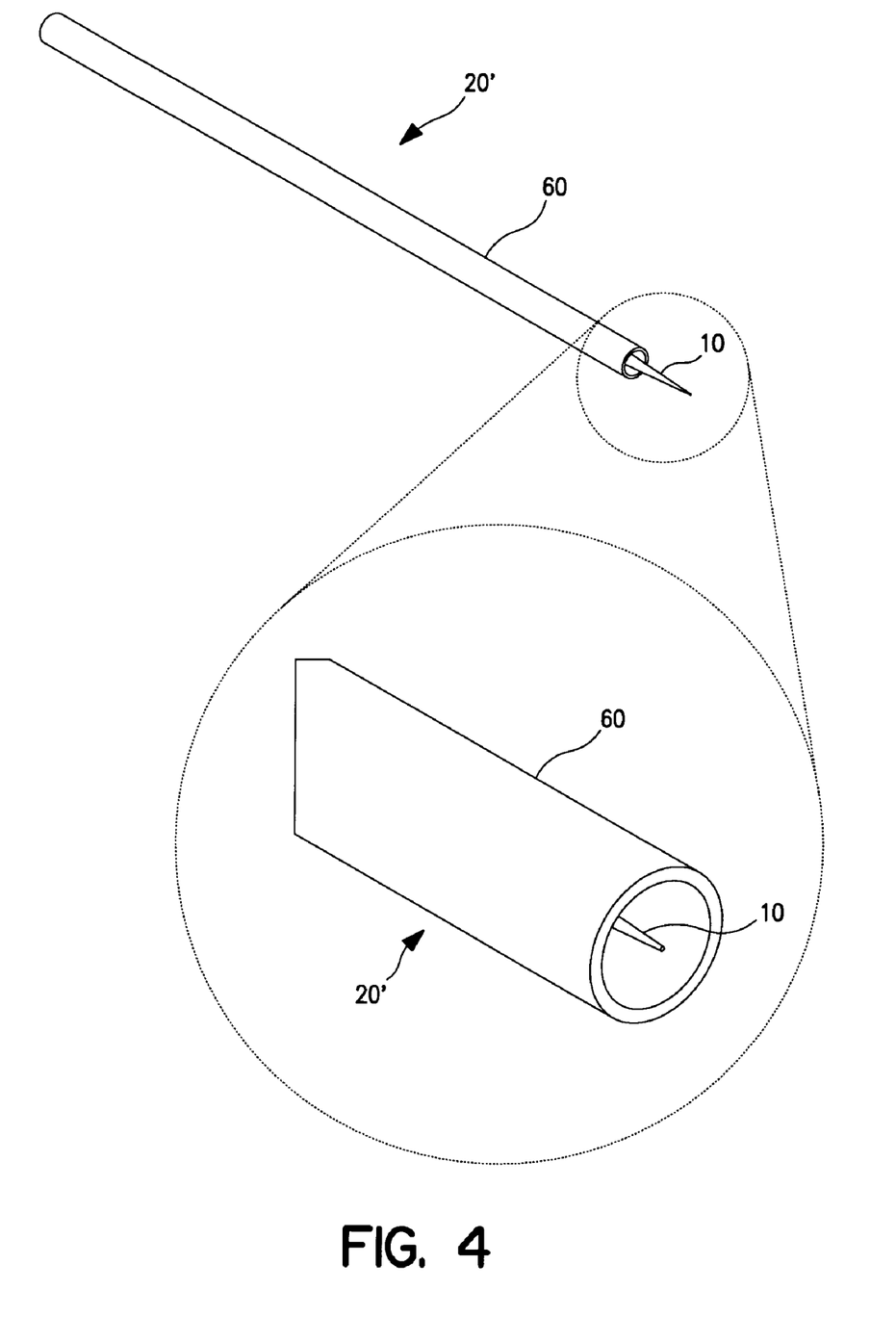
FIG. 4 illustrates a guarded assembly which includes a blunt tip pipette.

The guarded assembly 20' may use pipettes other than the bubble pipette 20, including a prior art blunt tip pipette 10, as shown in FIG. 4. Any surface suitable for sealing a cell may be disposed within the guarded assembly 20'—the surface need not be defined on a pipette. For example, a flat (or arcuate) surface may extend across the lumen of the guard pipette 60 having an aperture formed therethrough for sealing.

Figure 5:
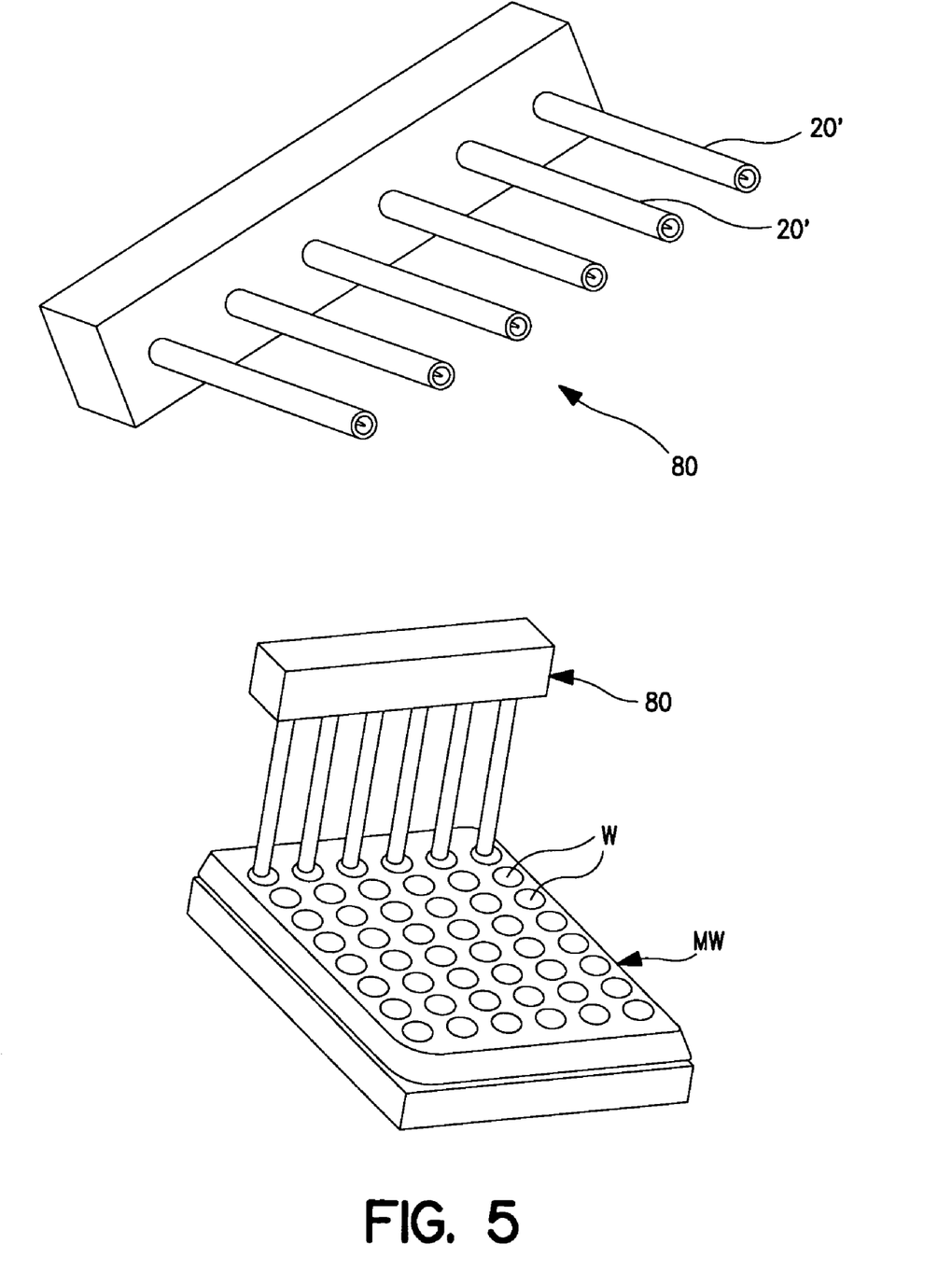
FIG. 5 is a diagram illustrating an array of pipettes in accordance with certain embodiments of the present invention.

Referring to FIG. 5, it is contemplated that an array 80 of pipettes may be provided to accomplish simultaneous and/or parallel cell contacting and seal formation in order to accomplish high throughput testing. The pipettes of the array 80 may be similar in configuration (e.g., an array entirely of bubble pipettes 20 or an array entirely of guarded assemblies 20'), or the array 80 may contain a variety of pipette configurations, including bubble pipettes 20, guarded assemblies 20', and/or pipettes 10 as found in existing technologies as shown representatively in FIG. 5. The pipettes may be secured in a series of substantially parallel rows, although other configurations for array 80 are readily contemplated and obvious to one of skill in the art. The array 80 may include pipettes each having separate coupling members (not shown) to form the array 80. Alternatively, a single member having multiple coupling elements (not shown) may be provided to secure the pipettes in place.

Figure 6:
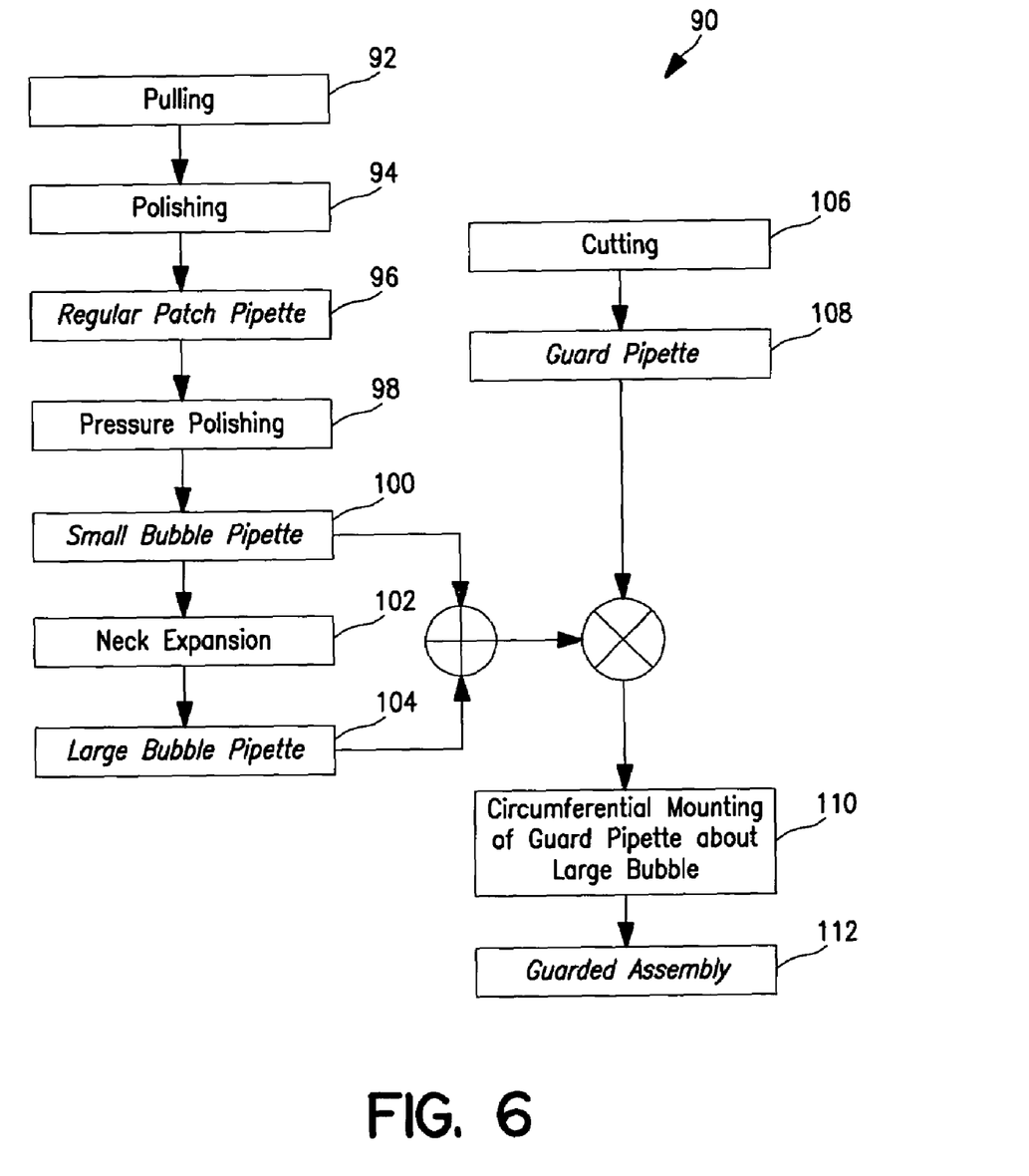
FIG. 6 is a flowchart illustrating exemplary steps for manufacturing pipettes of the present invention.

FIG. 6 displays an exemplary method 90 by which the pipette configurations (bubble pipette 20; guarded assembly 20') of the present invention may be manufactured. The process 90 begins at step 92 wherein a conventional pulling process is iteratively performed. Such process is described in Sakman and Neher, "Single Channel Recording", Plenum Publishing, 1995. As an example, a multi-stage horizontal pipette puller, such as the P-2000 manufactured by SUTTER INSTRUMENTS of Novarto, Calif., applies a series of iterative heating and pulling steps to stock (e.g., laboratory grade borosilicate glass (CORNING 7052) tubing with an internal diameter of 0.68 mm, an outer diameter of 1.2 mm, and a length of 100 mm) to form a conventional, unpolished, blunt tip pipette (e.g., a pipette having an ~1 µm inner diameter with a measurable resistance of 2–4 M$\Omega$ when filled with the normal saline solutions used during electrical recording).

Next, at step 94, a polishing process is performed. The polishing may be accomplished using a microforge, such as the MF-830 produced by NARISHIGE GROUP of East Meadow, N.Y. The microforge has a heating platinum point filament that produces a temperature sufficient to melt glass. The pipette tip is polished so as to shape and smooth the surface of the tip. After such polishing a conventional ("regular") pipette is formed (box 96).

Next, a pressure polishing step 98 is begun to expand the tip of the pipette to form a bubble at the tip of the pipette. Such pressure polishing is described in Goodman and Lockery, J. Neuroscience Methods, 100:13–15, 2000. In order to form a small bubble (having a dimension D of 5 to 10 µm) at the tip of the pipette, pressure of ~20 pounds-per-square-inch (p.s.i.) is applied through the distal end 30 of the pipette 20 with a point filament source heating the pipette tip in an iterative process under microscopic visual control, thereby forming a "small bubble" pipette (box 100) having a measurable resistance of ~1 M$\Omega$ when filled with the normal saline solutions used during electrical recording. However, in contrast to the Goodman and Lockery method, the small bubble formed hereby has no conical tip portion, wherein, as described above, the exterior surface 21 of the bubble 22 defines the tip of the pipette 20.

Figure 7:
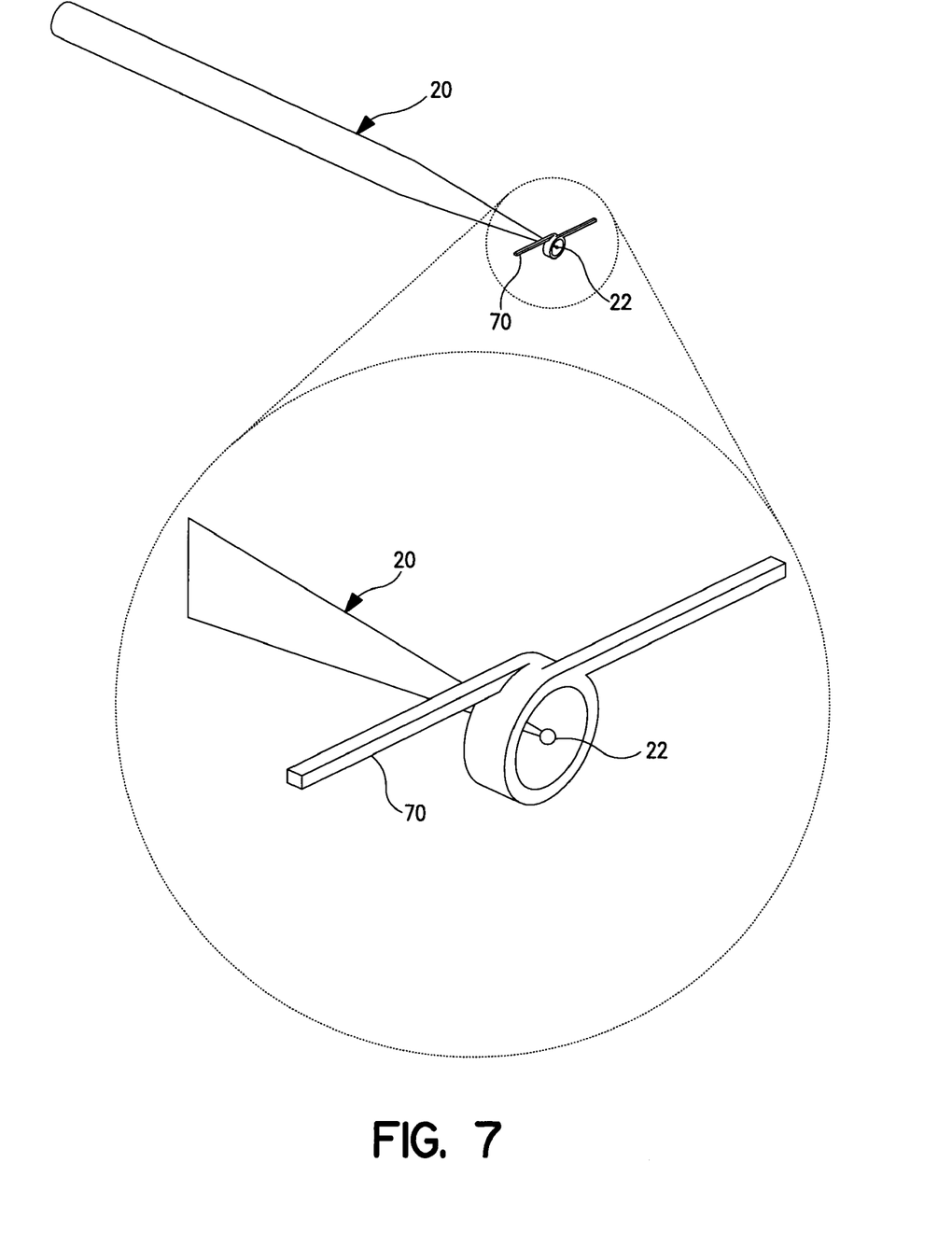
FIG. 7 is a schematic depicting a circular filament used in forming a micropipette of the subject invention.

A neck expansion step 102 may be provided to form large bubble pipettes (having a dimension D of up to 25 µm). This step involves increasing the back pressure up to ~50 p.s.i. and inserting the previously-formed small bubble 22 into a filament 70, which is preferably circular, where it is heated in an iterative process under microscopic visual control (FIG. 7). Although the filament 70 is depicted as being circular, other shapes are possible, such as, rectangular and triangular. Also, the filament 70 may be elongated to define a box or cylindrical shape. The filament 70 may be any shape that wholly, or at least substantially, encircles the pipette 20 adjacent to the bubble 22. The filament 70 is preferably positioned to heat the section of the pipette adjacent to the bubble 22 (e.g., with reference to FIG. 2, section 28c). The process results in a "large bubble" pipette (box 104).

To form the guarded assembly 20', an existing stock of suitable pipette tubing (having an outer diameter of 1.65 mm, an inner diameter of 1.28 mm, and a length of 100 mm) of sufficient length and diameter is cut using a diamond knife or the like (step 106), thereby forming predetermined (e.g., 15–30 mm) lengths of guard pipette 60 (box 108). The ends of the guard pipette 60 are fire-polished, and the guard pipette 60 is circumferentially mounted around the bubble pipette 20 (step 110). Thereafter, the guard pipette 60 and the bubble pipette 20 may be relatively adjusted to obtain a desired overlap. The guard pipette 60 may then be rigidly secured to the bubble pipette 20 by placing an adhesive therebetween at a desired point, preferably on the hollow tubular section of the bubble pipette 20, or using any other technique known to those skilled in the art. Alternatively, the guard pipette 60 is not rigidly secured, but allowed to slide relative to the bubble pipette 20. It is preferred that the guard pipette 60 have an interior diameter which is slightly greater than the exterior of the bubble pipette 20 (e.g., at the section 28a) to allow for snug interaction. It is preferred that the joint between the bubble pipette 20 and the guard pipette 60 be sealed for upright use, since sealant is important for formation of a volume of liquid with the appropriate volume. Guarded assemblies 20' intended for inverted use, as described below, are preferably sealed using any material and technique known to those skilled in the art, such as silicon sealant. In either such manner, a guarded assembly 20' is formed (box 112).

Figure 8:
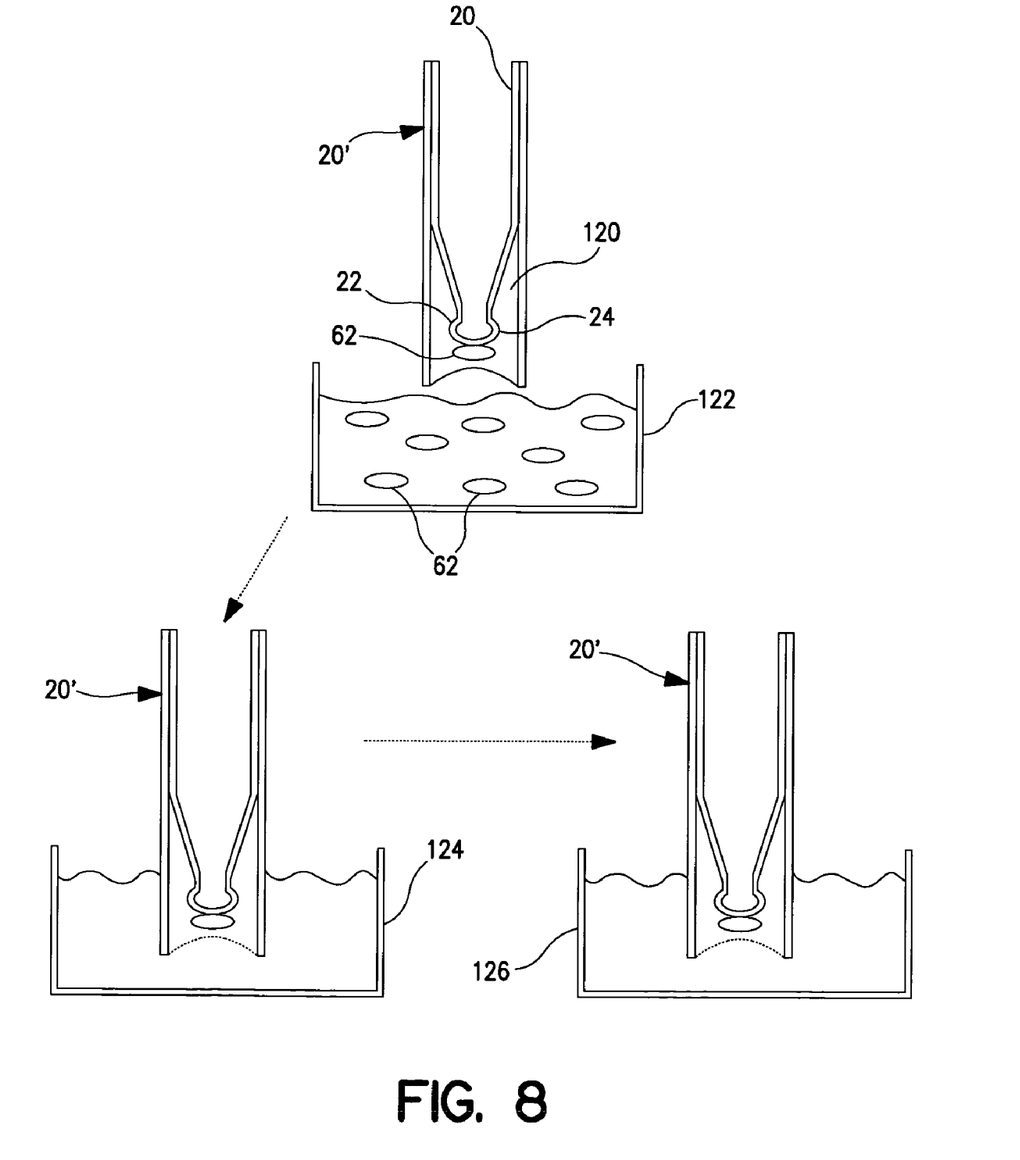
FIG. 8 is a diagram illustrating a first method of screening compounds using the subject invention.
Figure 9:
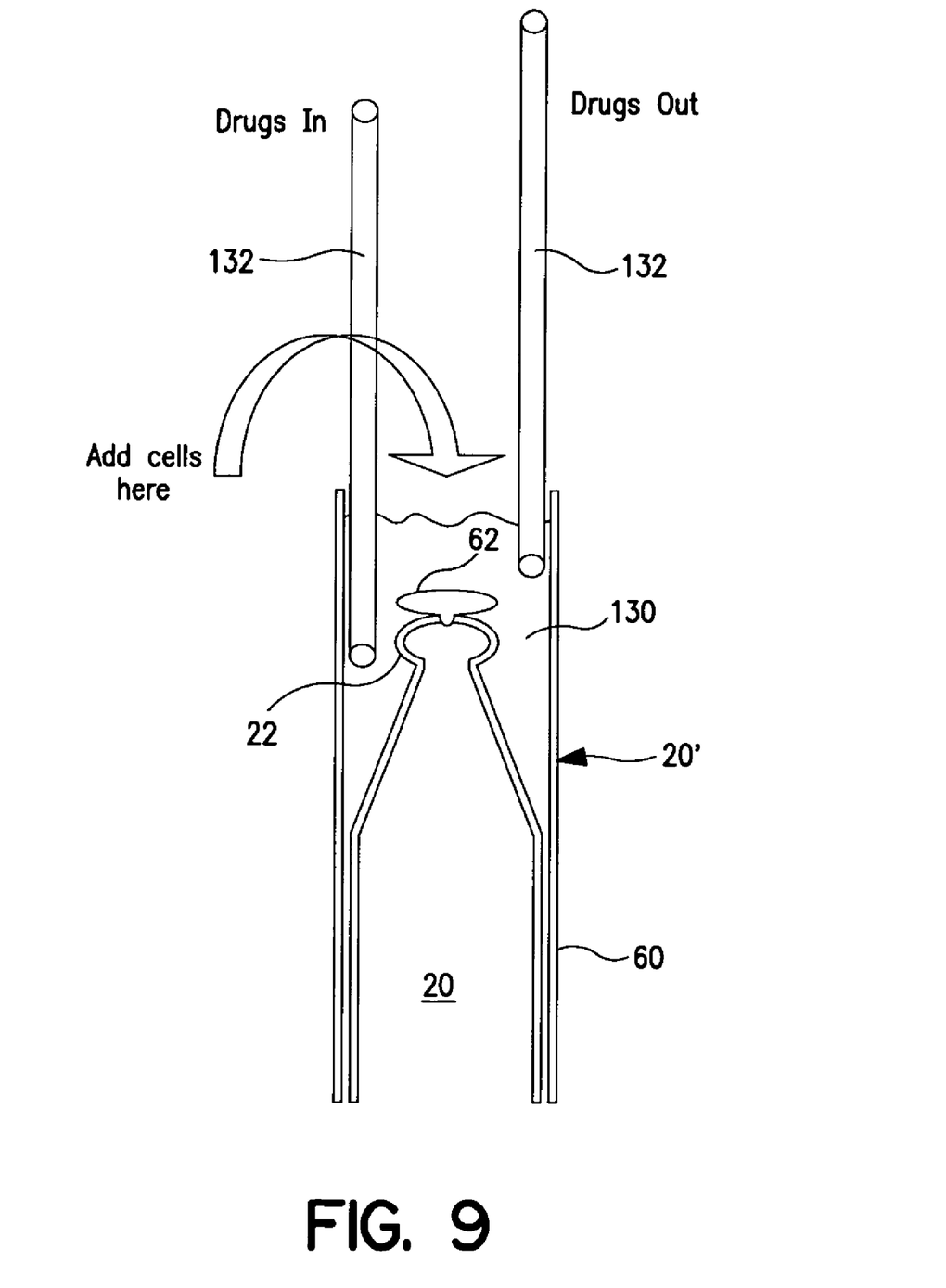
FIG. 9 is an illustration of a second method of screening compounds using the subject invention.
Figure 10:
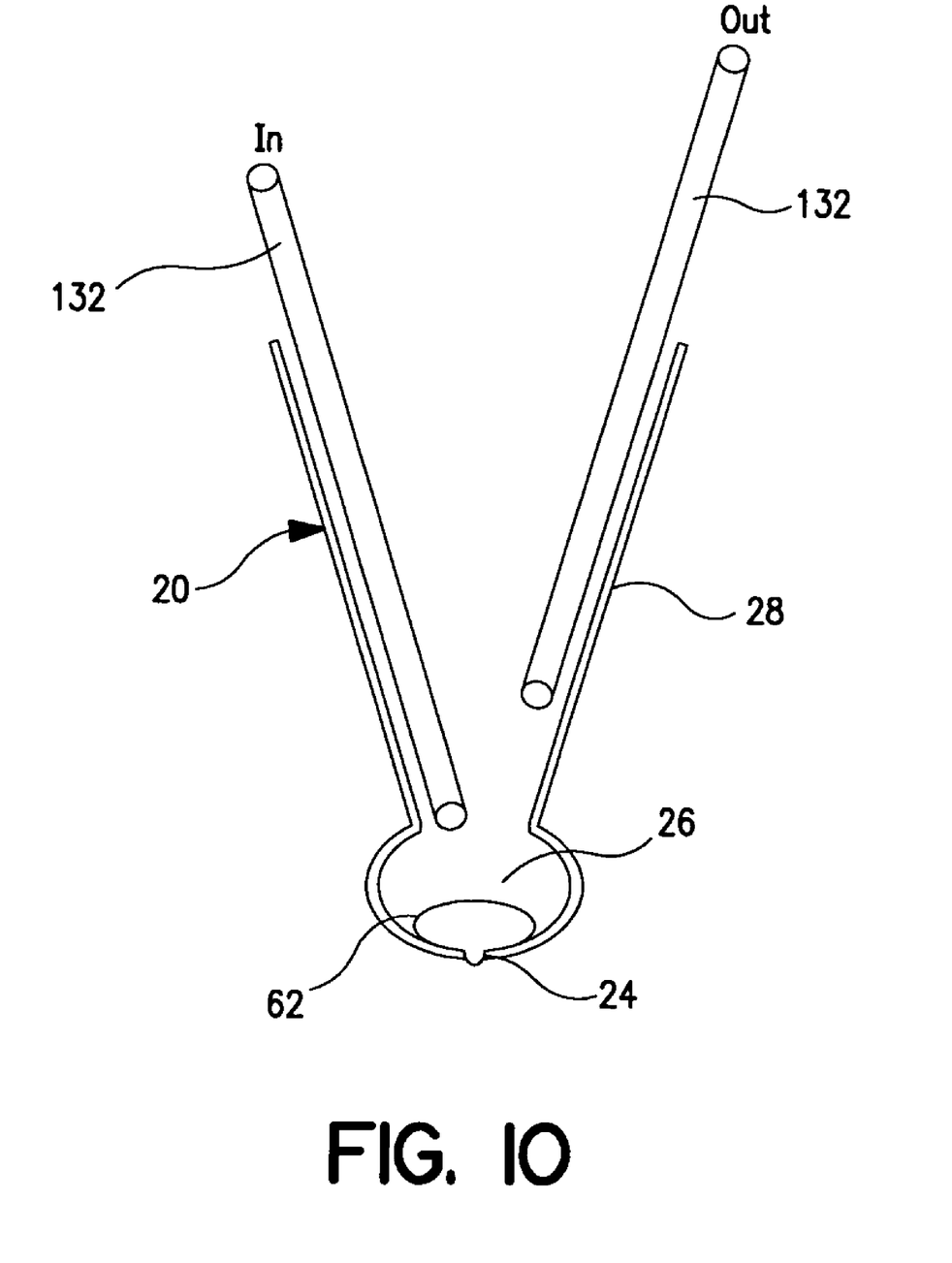
FIG. 10 is an illustration of a third method of screening compounds using the subject invention.

FIGS. 8–10 depict various methods for accomplishing electrophysiological measurements of cells (whole cell or on cell) for screening compounds using a pipette or an array of pipettes of the invention. Referring to FIG. 8, a first method is depicted, wherein a bubble pipette 20 is introduced into a cell population, such as in a moving stream, or a well 122 (of a multiwell plate). Any technique available may be used to allow the bubble 22, particularly in the region of the aperture 24, to contact a cell, connect to it, and facilitate seal formation (e.g., introducing negative pressure in the bubble pipette 20; generating an electrical field at the bubble 22 to attract a cell ("electrofocusing")). Preferably, the guarded assembly 20' is used in this method so that a volume of liquid 120 may be formed to wholly encompass a cell 62 connected to the bubble pipette 22. With an acceptable seal being formed between the cell 62 and the bubble pipette 20, the volume of liquid 120 acts to maintain the electrical and mechanical stability of the seal. The guarded assembly 20' may then be sequentially introduced to one or more baths 124, 126 after seal formation. Using conventional techniques, electrophysiological properties of the cell 62 may be evaluated in determining the effect of various compounds on the cell 62.

Referring now to FIG. 9, in a second method, the guarded assembly 20' is inverted after cell contacting and seal formation is accomplished. A fluid suspension or the like may next be introduced in the cup-shaped reservoir 130 defined by the guard pipette 60 and the pipette 20 using, for example, a series of micro-needles or capillaries 132. A cell population is dispersed throughout the fluid suspension such that a cell 62 comes into contact with, and is sealed to, the bubble 22 using any known technique, as indicated above. Various compounds may be introduced into the reservoir 130 for screening.

Referring to FIG. 10, a third method may be accomplished where testing occurs within the interior chamber 26 of the bubble pipette 20. Here, the pipette 20 is upright with the bubble 22 being located gravitationally below the tubular section 28. A fluid suspension or the like is introduced into the interior chamber 26 through the hollow tubular section 28 using micro-needles or capillaries 132, which includes a cell population. One of the cells 62 will settle onto, or may be drawn to, the aperture 24 by negative pressure applied externally of the aperture 24 or through electrofocusing. Once the cell 62 contacts the aperture 24, an acceptable seal may be formed using known techniques. Various compounds may be introduced into the interior chamber 26 via the tubular section 28.

The above-described methods can be practiced with individual pipettes 20, guarded assemblies 20', or in any form, such as the array 80. With array form, parallel screening may be achieved where large populations of cells may be simultaneously screened. For example, as shown in FIG. 5, the array 80 may be used with a multiwell plate MW to simultaneously screen one or more compounds in the wells W of the plate MW. In addition, whole cell testing can be achieved via the additional step(s) of electroporation or additional negative pressure or perforated patch "chemopermeabilization" or a combination thereof.

Figure 11:
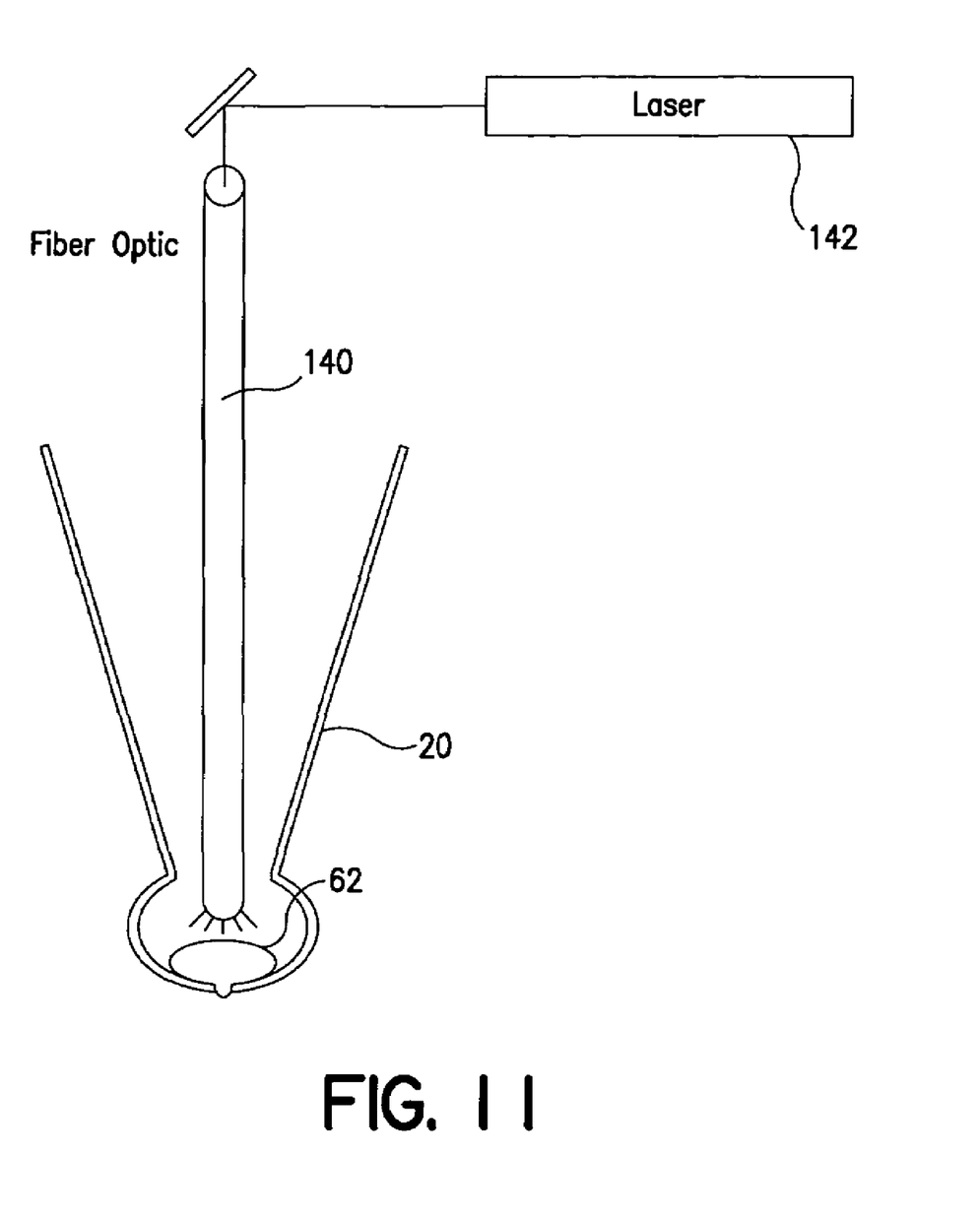
FIG. 11 is an illustration of an exemplary application of optical stimulation and recording in accordance with the present invention; and, FIG. 12 is an illustration of an exemplary apparatus for amperometry in accordance with the present invention.

In addition to testing electrophysiological characteristics, with respect to any of the above-identified methods, it may be desirable to activate or deactivate certain test compounds which affect ion channel behavior using optical stimulation. Referring to FIG. 11, an optical stimulation apparatus, such as a fiber optic line 140 in communication with a laser 142, may be inserted in the distal end of a bubble pipette 20. Light can then be delivered to the sealed cell 62 in a specific and localized manner.

Optical recording can be accomplished in a similar manner to electrophysiological testing with similar equipment. Such a process is useful, for example, in monitoring fluorescence indicators useful for tracking cellular calcium. To accomplish this, excitation light could be delivered via the optical fiber 140. A collection lens (not shown) could be placed at the end of the optic fiber near the tip of the pipette 20 to collect fluorescence and transmit the same via the optic fiber 140 to an external recording apparatus (not shown)

Figure 12:
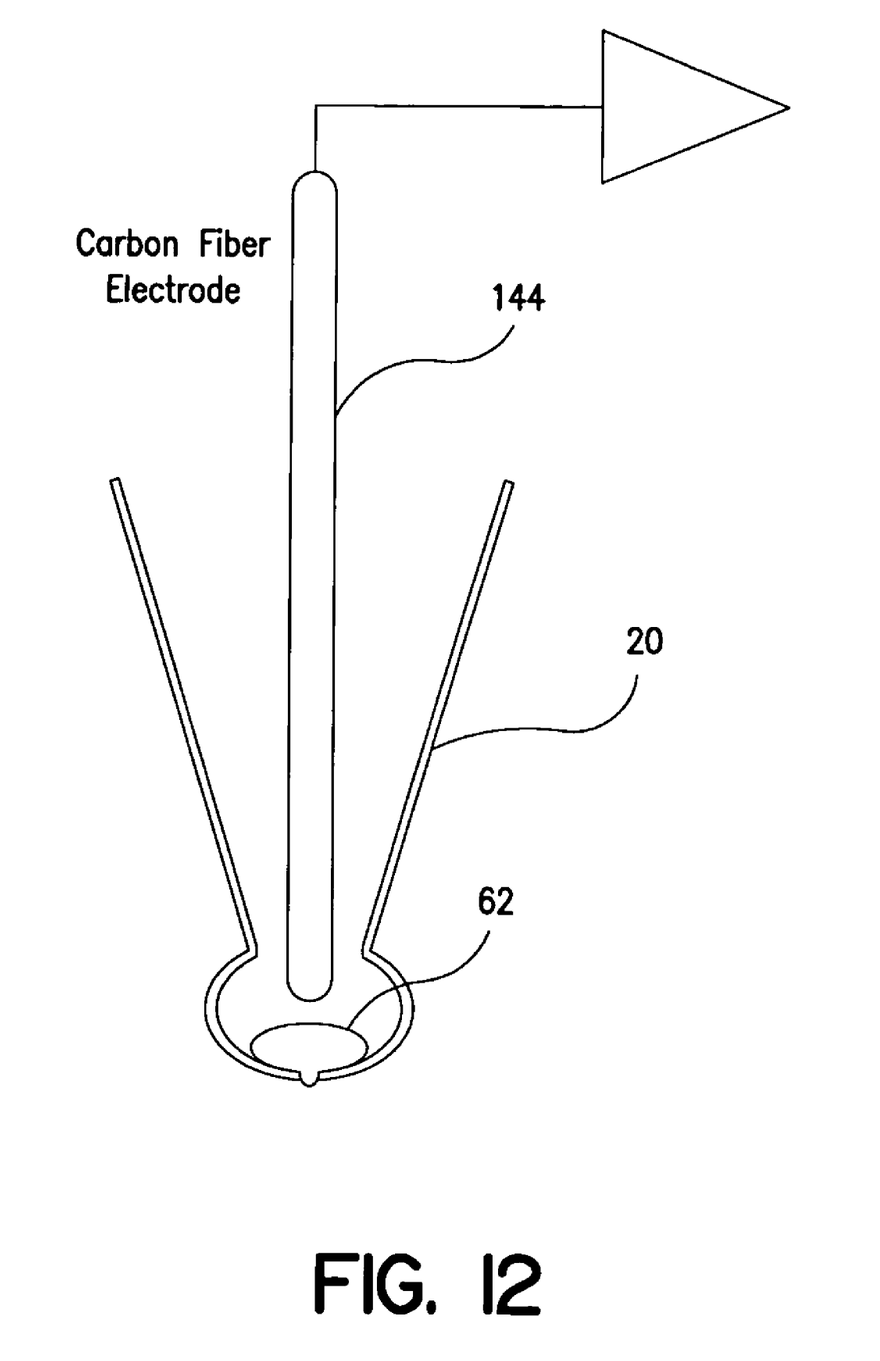

Furthermore, with reference to FIG. 12, a carbon fiber microelectrode 144 (<10 μm) may be placed inside the pipette 20 or guarded assembly 20' for electrochemical detection (amperometry) with the sealed cell 62. This type of sensing is possible from any kind of oxidizable compound, such as catecholamines (e.g., epinephrine, norepinephrine and dopamine), indolamines (e.g., serotonin) and other oxidizable compounds. Detection of these kinds of compounds could provide potentially important information about synaptic transmission and excitation-secretion coupling.

While the invention has been described in relation to the preferred embodiments with several examples, it will be understood by those skilled in the art that various changes may be made without deviating from the spirit and scope of the invention as defined in the appended claims.

What is claimed is:

1. A pipette, comprising:
    hollow tube having a distal end, a proximal tip end, and a bulbous bubble portion forming an interior chamber, the bubble portion being located at the proximalmost portion of the hollow tube and defining the tip end with an arcuate shaped exterior surface facing generally in the proximal direction, wherein no portion of said hollow tube extends proximally from said tip end, and wherein the bubble portion having an aperture extending through said exterior surface of the bubble portion and into communication with the interior chamber, said aperture being smaller in diameter than said interior chamber, portions of said exterior surface adjacent to said aperture being smooth and coextensive with other portions of said exterior surface, and
    wherein at least the bubble portion comprises a glass material.

2. The pipette of claim 1, wherein the hollow tube has a tapered section disposed between the distal end and the bubble portion, wherein the tapered section converges in a direction towards said bubble portion.

3. The pipette of claim 2, wherein the hollow tube has a second section of continuous diameter disposed between the distal end and the tapered section.

4. The pipette of claim 1, wherein the hollow tube including a section of substantially continuous diameter disposed between the distal end and the bubble portion.

5. The pipette of claim 1, wherein the aperture is disposed at the proximalmost portion of the bubble portion.

6. The pipette of claim 1, wherein the bubble portion defines an outer dimension of 25 μm or less.

7. The pipette of claim 6, wherein the outer dimension is 10 μm or less.

8. The pipette of claim 1, wherein a cross-section of the bubble portion is substantially circular.

9. The pipette of claim 1, wherein a cross-section of the bubble portion is substantially oval.

10. The pipette of claim 1, wherein at least a section of the bubble portion is substantially spherical.

11. The pipette of claim 1, wherein at least a section of the bubble portion is substantially ovuloid.

12. The pipette of claim 1, wherein the interior chamber is in communication with other portions of the hollow tube.

13. The pipette of claim 1, wherein the bubble portion defines an external dimension greater than an adjacent portion of the hollow tube.

14. A pipette assembly comprising:
    a hollow tube having a distal end, a tip end, and a bulbous bubble portion forming an interior chamber, the bubble portion defining the tip end, wherein the bubble portion further having an aperture extending through an exterior surface of the bubble portion and into communication with the bubble portion and the interior chamber; and
    a guard pipette including an open proximal end, said guard pipette circumferentially at least partially enclosing the bubble portion, wherein the tip end is exposed through the open proximal end of the guard pipette.

15. The pipette assembly of claim 14, wherein the guard pipette extends from said hollow tube and beyond the bubble portion.

16. The pipette assembly of claim 14, wherein the guard pipette is at least coextensive in length with said hollow tube.

17. The pipette assembly of claim 14, wherein an interior diameter of the guard pipette is substantially equal to an exterior diameter of the hollow tube.

18. The pipette assembly of claim 14, wherein the guard pipette is movable relative to the hollow tube, thereby being extendable a variable distance beyond the bubble portion.

19. The pipette assembly of claim 14, wherein the guard pipette comprises a glass material.

20. The pipette assembly of claim 14, wherein portions of said exterior surface adjacent to said aperture being smooth and coextensive with other portions of said exterior surface.

21. The pipette assembly of claim 14, wherein the bubble portion defines an external dimension greater than an adjacent portion of the hollow tube.

22. The pipette of claim 1, wherein said portions of said exterior surface adjacent to said aperture are non-flat.

23. The pipette of claim 1, wherein the aperture defines an opening with a dimension in the range of 0.5–3.0 microns.

24. The pipette assembly of claim 14, wherein portions of said exterior surface adjacent to said aperture are non-flat.

25. The pipette assembly of claim 14, wherein the aperture defines an opening with a dimension in the range of 0.5–3.0 microns.

26. The pipette assembly of claim 14, wherein at least the bubble portion of the hollow tube comprises a glass material.

27. The pipette assembly of claim 19, wherein at least the bubble portion of the hollow tube comprises a glass material.

28. The pipette assembly of claim 14, wherein the tip end is a proximal end of the hollow tube, the bubble portion being located at the proximalmost portion of the hollow tube.

29. A pipette, comprising:
hollow tube having a distal end, a proximal tip end, and a bulbous bubble portion forming an interior chamber, the bubble portion being located at the proximalmost portion of the hollow tube and defining the tip end, wherein the bubble portion having an aperture extending through an exterior surface of the bubble portion and into communication with the interior chamber, portions of said exterior surface adjacent to said aperture being smooth and coextensive with other portions of said exterior surface, and
wherein the aperture has a diameter in the range of 0.5–3 microns.

30. The pipette of claim 29, wherein at least the bubble portion comprises a glass material.

31. The pipette of claim 29, wherein the hollow tube has a tapered section disposed between the distal end and the bubble portion, wherein the tapered section converges in a direction towards said bubble portion.

32. The pipette of claim 31, wherein the hollow tube has a second section of continuous diameter disposed between the distal end and the tapered section.

33. The pipette of claim 29, wherein the hollow tube including a section of substantially continuous diameter disposed between the distal end and the bubble portion.

34. The pipette of claim 29, wherein the aperture is disposed at the proximalmost portion of the bubble portion.

35. The pipette of claim 29, wherein the bubble portion defines an outer dimension of 25 µm or less.

36. The pipette of claim 35, wherein the outer dimension is 10 µm or less.

37. The pipette of claim 29, wherein a cross-section of the bubble portion is substantially circular.

38. The pipette of claim 29, wherein a cross-section of the bubble portion is substantially oval.

39. The pipette of claim 29, wherein at least a section of the bubble portion is substantially spherical.

40. The pipette of claim 29, wherein at least a section of the bubble portion is substantially ovuloid.

41. The pipette of claim 29, wherein the interior chamber is in communication with other portions of the hollow tube.

42. The pipette of claim 29, wherein the bubble portion defines an external dimension greater than an adjacent portion of the hollow tube.

43. The pipette of claim 29, wherein said portions of said exterior surface adjacent to said aperture are non-flat.

44. The pipette assembly of claim 14, wherein the aperture is disposed at the proximalmost portion of the bubble portion.

45. The pipette assembly of claim 14, wherein said aperture being smaller in diameter than said interior chamber.

46. The pipette of claim 29, wherein said aperture being smaller in diameter than said interior chamber.

* * * * *